(12) United States Patent
Abe (10) Patent No.: US 8,649,482 B2
(45) Date of Patent: Feb. 11, 2014

(54) X-RAY IMAGING APPARATUS

(75) Inventor: Masahiro Abe, Yamato (JP)

(73) Assignee: Canon Kabushiki Kaisha, Tokyo (JP)

(*) Notice: Subject to any disclaimer, the term of this patent is extended or adjusted under 35 U.S.C. 154(b) by 315 days.

(21) Appl. No.: 13/206,868

(22) Filed: Aug. 10, 2011

(65) Prior Publication Data

US 2012/0051519 A1 Mar. 1, 2012

(30) Foreign Application Priority Data

Aug. 31, 2010 (JP) ................................ 2010-195060

(51) Int. Cl.
*H05G 1/64* (2006.01)

(52) U.S. Cl.
USPC .............................................. 378/98; 378/91

(58) Field of Classification Search
None
See application file for complete search history.

(56) References Cited

U.S. PATENT DOCUMENTS

2008/0275349 A1* 11/2008 Halperin et al. ............... 600/484
2012/0112747 A1* 5/2012 Alexiuk et al. ............... 324/318

FOREIGN PATENT DOCUMENTS

JP 2003-210444 7/2003

\* cited by examiner

*Primary Examiner* — Hoon Song
*Assistant Examiner* — Danielle Fox
(74) *Attorney, Agent, or Firm* — Fitzpatrick, Cella, Harper & Scinto (57) ABSTRACT

An X-ray imaging apparatus that performs X-ray imaging while switching a plurality of wireless sensors according to an imaging condition of an object includes: an acquisition unit that acquires examination information indicating the imaging condition of the object; a management unit that manages, as sensor information, remaining battery levels of the plurality of wireless sensors that have been registered; a control unit that assigns a priority order of wireless sensor candidates usable for performing the X-ray imaging according to the imaging condition indicated in the acquired examination information to the plurality of wireless sensors, in descending order of the remaining battery levels; and an imaging unit that performs the X-ray imaging of the object using wireless sensors sequentially consisting of those in descending order of the priority order assigned by the control unit up to a wireless sensor having a preset order number, as determined according to the imaging condition.

9 Claims, 7 Drawing Sheets

| IMAGING REGION | IMAGING EQUIPMENT |
|---|---|
| FRONT CHEST | STAND |
| SIDE CHEST | STAND |
| FRONT HEAD | TABLE |
| FRONT ABDOMEN | STAND |

FIG. 4B

| IMAGING REGION | IMAGING EQUIPMENT | GRID CONDITION |
|---|---|---|
| FRONT CHEST | STAND | YES |
| SIDE CHEST | STAND | YES |
| FRONT HEAD | TABLE | YES |
| FRONT ABDOMEN | STAND | NO |

FIG. 4C

| IMAGING REGION | IMAGING EQUIPMENT | IMAGING AREA SIZE |
|---|---|---|
| FRONT CHEST | STAND | 40cm × 40cm |
| SIDE CHEST | STAND | 30cm × 40cm |
| FRONT HEAD | TABLE | 20cm × 25cm |
| FRONT ABDOMEN | STAND | 40cm × 40cm |

FIG. 5A

| WIRELESS SENSOR NAME | SERIAL NUMBER | COMMUNICATION CONDITION | REMAINING BATTERY LEVEL |
|---|---|---|---|
| AAA | 00108022 | ONLINE | 20% |
| BBB | 02311234 | ONLINE | 50% |
| CCC | 06003411 | ONLINE | 80% |

FIG. 5B

| WIRELESS SENSOR NAME | SERIAL NUMBER | COMMUNICATION CONDITION | COMMUNICATION MODE | REMAINING BATTERY LEVEL |
|---|---|---|---|---|
| AAA | 00108022 | ONLINE | WIRED, WIRELESS | 20% |
| BBB | 02311234 | ONLINE | WIRELESS | 50% |
| CCC | 06003411 | ONLINE | WIRELESS | 80% |

FIG. 5C

| WIRELESS SENSOR NAME | SERIAL NUMBER | COMMUNICATION CONDITION | REMAINING BATTERY LEVEL | READING SIZE |
|---|---|---|---|---|
| AAA | 00108022 | ONLINE | 20% | 43cm × 43cm |
| BBB | 02311234 | ONLINE | 50% | 23cm × 28cm |
| CCC | 06003411 | ONLINE | 80% | 43cm × 43cm |

X-RAY IMAGING APPARATUS

BACKGROUND OF THE INVENTION

1. Field of the Invention

The present invention relates to an X-ray imaging apparatus for imaging a medical X-ray image.

2. Description of the Related Art

Conventionally, X-ray sensors that convert X-rays into digital images and output the digital images are generally connected by cables. However, with recent advances in radio techniques, a wireless sensor has been debuted, and imaging is being performed more and more without the use of cables. As a conventional example of these techniques, for example, there is a technique disclosed in Japanese Patent Laid-Open No. 2003-210444.

In a digital X-ray imaging system, a control unit and an operation unit are required to perform imaging while switching a plurality of sensor units as appropriate. In the case of conventional cable-connected sensor units, a sensor unit that is connected with a cable and can perform communication is a currently usable sensor, and a sensor used for imaging is uniquely selected. Meanwhile, in the case where a plurality of wireless sensors have been registered into an imaging system and all of the sensors can perform communication, a sensor to be used cannot be uniquely selected. Thus, an operator has to determine a wireless sensor to be used.

However, it is difficult for an operator (e.g., an engineer, a doctor, etc.) to know the statuses of the respective wireless sensors and properly determine a wireless sensor to be used. Thus, for example, there have been cases in which, after a sensor has been selected and an examination has been started, the sensor selected first has to be switched with another sensor during the examination because the remaining battery level is not sufficient. In such a case, the examination has to be temporarily halted to exchange sensors, which lowers the efficiency of the examination. Additionally, this is disadvantageous also for the patient because the patient is kept waiting for sensors to be exchanged. Furthermore, when used on a mobile cart, the cart is moved with one sensor mounted thereon, and, thus, even when a plurality of sensors have been registered into a system, one sensor has to be selected so as to be repeatedly used. Moreover, in the case where imaging in the upright position and the supine position can be performed using two wireless sensors, sensors are selected on an empirical basis such that one sensor is assigned to do upright position imaging, and the other to do supine position imaging. Accordingly, the operation is not always efficient.

SUMMARY OF THE INVENTION

In view of the above-described problems, the present invention provides an X-ray imaging technique that can determine a usable wireless sensor in each imaging condition from among a plurality of wireless sensors.

According to one aspect of the present invention, there is provided an X-ray imaging apparatus that performs X-ray imaging while switching a plurality of wireless sensors according to an imaging condition of an object, comprising: an acquisition unit configured to acquire examination information indicating the imaging condition of the object; a management unit configured to manage, as sensor information, remaining battery levels of the plurality of wireless sensors that have been registered; a control unit configured to assign a priority order of wireless sensor candidates usable for performing the X-ray imaging according to the imaging condition indicated in the examination information acquired by the acquisition unit to the plurality of wireless sensors, in descending order of the remaining battery levels managed by the management unit; and an imaging unit configured to perform the X-ray imaging of the object using wireless sensors sequentially consisting of those in descending order of the priority order assigned by the control unit up to a wireless sensor having a preset order number, as determined according to the imaging condition.

According to the present invention, it is possible to determine a usable wireless sensor in each imaging condition from among a plurality of wireless sensors.

Further features of the present invention will become apparent from the following description of exemplary embodiments with reference to the attached drawings.

DESCRIPTION OF THE EMBODIMENTS

First Embodiment

Hereinafter, a hardware configuration of an X-ray imaging apparatus according to a first embodiment of the present invention will be described with reference to FIG. 1. A control unit 101 includes a RAM 1010, a ROM 1011, a network interface (a LAN/IF 1012), a DISK/IF 1013, a CPU 1014, and a non-volatile storage device 1015 such as a hard disk. The constituent elements of the control unit 101 are connected to each other via a system bus 1016, and are configured so as to realize the function of a commonly used information processing apparatus.

The control unit 101 drives sensor units or controls an X-ray generation unit 104 based on input from an operator via an operation unit 106. Furthermore, the control unit 101 manages data such as correction data, X-ray imaging conditions, and image data using a database.

The operation unit 106 is configured from input devices such as a mouse, a keyboard, and an irradiation switch, and is used by the operator for inputting various types of commands or data to the control unit 101. A display unit 105 is configured from a commonly used monitor such as a CRT or liquid crystal display, and displays data such as image data or a graphical user interface (GUI) on a screen.

The X-ray generation unit 104 (X-ray generator) generates X-rays that are to be irradiated onto an object. An imaging unit 110 has a first sensor unit 102 and a second sensor unit 103, and performs X-ray imaging of the object using the first sensor unit 102 or the second sensor unit 103. Here, assignment of sensor units used for X-ray imaging will be described later in detail. The first sensor unit 102 and the second sensor unit 103 are sensor units that convert an X-ray signal transmitted through the object into an image and output the image, and the converted image is transferred from the first sensor unit 102 and the second sensor unit 103 to the control unit 101.

Figure 1:
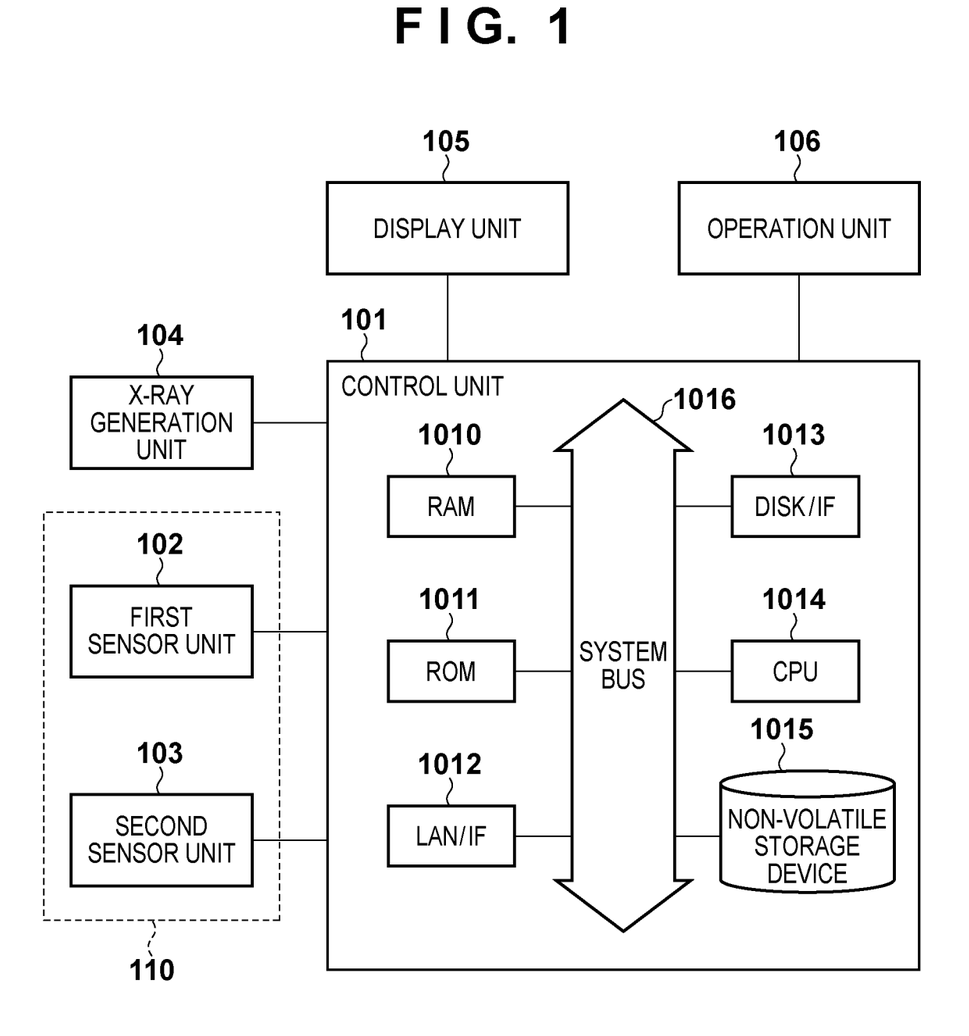
FIG. 1 is a hardware configuration diagram of an X-ray imaging apparatus according to a first embodiment.

In the example in FIG. 1, two sensor units are shown, but the number of sensor units is not limited to two, and three or more sensor units may be connected. Note that connection of the control unit 101 to the first sensor unit 102, the second sensor unit 103, the X-ray generation unit 104, the display unit 105, and the operation unit 106 may be either wired or wireless. Furthermore, any communication protocol may be used, and any communication forms may be adopted.

Figure 2:
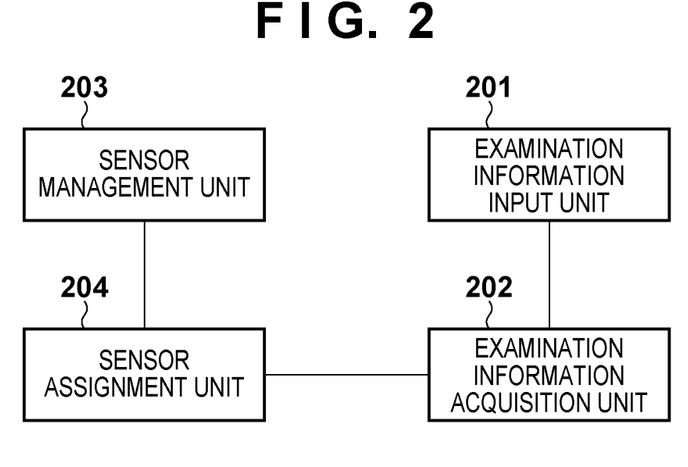
FIG. 2 is a functional configuration diagram of the X-ray imaging apparatus according to the first embodiment.

Next, a functional configuration of the X-ray imaging apparatus of this embodiment will be described with reference to FIG. 2. An examination information input unit 201 is used to input examination information indicating imaging conditions of an examination (X-ray imaging) that is about to be performed on the object. The examination information is input by the operator, for example, selecting imaging technique buttons displayed on the display unit 105 using input devices such as a mouse or a keyboard of the operation unit 106. Alternatively, the examination information may be input through an operation that receives examination request information (work list) from a radiology information system (RIS) and selects the examination request information. The examination information contains, for example, region information of imaging that is to be performed, orientation information, imaging area size, model number of a sensor to be used, information on equipment such as a table and a stand to be used for imaging, and grid condition of whether or not to perform imaging using a grid for removing scattered X-rays.

An examination information acquisition unit 202 acquires the examination information input by the examination information input unit 201. A sensor management unit 203 has a function of managing information and status of sensors registered into the X-ray imaging apparatus, and manages information indicating communication settings of each wireless sensor, communication condition of whether or not wireless communication is possible, remaining battery level, and the like. A sensor assignment unit 204 performs assignment control that assigns a proper wireless sensor to each imaging operation based on the content of the examination information acquired by the examination information acquisition unit 202 and the sensor information collected by the sensor management unit 203. The sensor assignment unit 204 assigns a priority order of wireless sensor candidates usable for performing X-ray imaging in an imaging condition indicated by the examination information to the plurality of wireless sensors managed by the sensor management unit 203, in descending order of the remaining battery level. Then, X-ray imaging of the object is performed using wireless sensors sequentially consisting of those in descending order of the assigned priority order up to a wireless sensor having a preset order number, as determined according to the imaging condition. If the number of wireless sensors to be used for X-ray imaging is one (if the preset order number is 1), a wireless sensor of the first priority order having the highest priority order is selected. If the number of wireless sensors to be used for X-ray imaging is two (if the preset order number is 2), the wireless sensor of the first priority order having the highest priority order and a wireless sensor of the second priority order having the second highest priority order (the preset order number is 2) are selected. Wireless sensors of the third priority order and subsequent priority orders are excluded from the selection targets. Here, the preset order number is determined according to the imaging condition or the like, and can be changed according to the imaging condition if the imaging condition such as an imaging environment changes.

Figure 3:
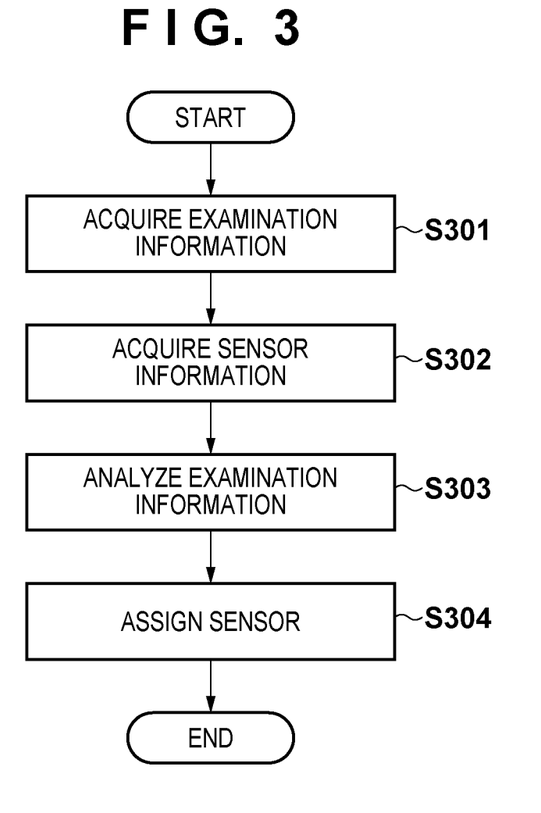
FIG. 3 is a chart illustrating an operation flow of the X-ray imaging apparatus according to the first embodiment.
Figure 4A:
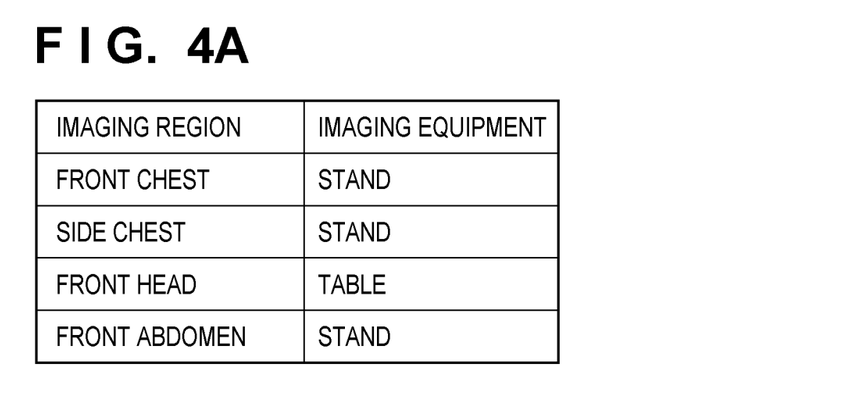
FIGS. 4A to 4C are tables illustrating examination information as an example.

Next, an operation flow of the X-ray imaging apparatus according to this embodiment will be described with reference to FIGS. 3, 4A to 4C, and 5A to 5C. This processing is performed under the overall control of the control unit 101. This flow illustrates a typical processing procedure from acquisition of examination information to assignment of sensors. First, in step S301, the examination information acquisition unit 202 acquires examination information. Generally, this process is performed immediately before starting the examination, and examination information as shown in FIG. 4A is acquired. The examination information contains, for example, information on an imaging region of the object and imaging equipment to be used for imaging of the imaging region. The imaging orientation of the object is determined by the information on the imaging equipment.

Figure 5A:
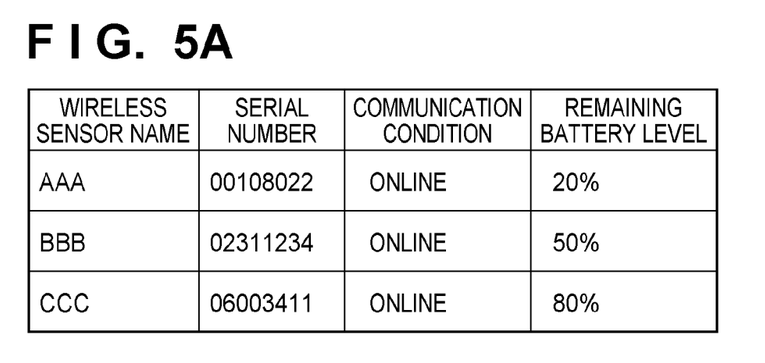
FIGS. 5A to 5C are tables illustrating sensor information as an example.

In step S302, the sensor assignment unit 204 acquires sensor information managed by the sensor management unit 203. In this step, for example, information indicating wireless sensor name, wireless sensor serial number, communication condition, and remaining battery level that has been registered into the system as shown in FIG. 5A is acquired. Here, the order of step S301 and S302 is not limited to this, and the examination information may be acquired after the sensor information has been acquired.

In step S303, the sensor assignment unit 204 analyzes the examination information acquired in step S301. The analysis of the examination information refers to the counting or collecting of information on the number of imaging operations, the region and the orientation in each imaging operation, equipment such as a table and a stand to be used, the information being contained in the examination information.

In step S304, the sensor assignment unit 204 assigns a wireless sensor to be used to each imaging operation based on the content analyzed in step S303 and the sensor information acquired in step S302. For example, the case will be assumed in which the information shown in FIGS. 4A and 5A is acquired. In this case, in step S304, the wireless sensor with the serial number 06003411 having the highest remaining battery level is assigned to imaging using a stand having the largest number of imaging operations (first priority order) when used as imaging equipment for imaging of the front chest, the side chest, and the front abdomen. Furthermore, the wireless sensor with the serial number 02311234 having the second highest remaining level is assigned to imaging using a table (second priority order).

Figure 4B:
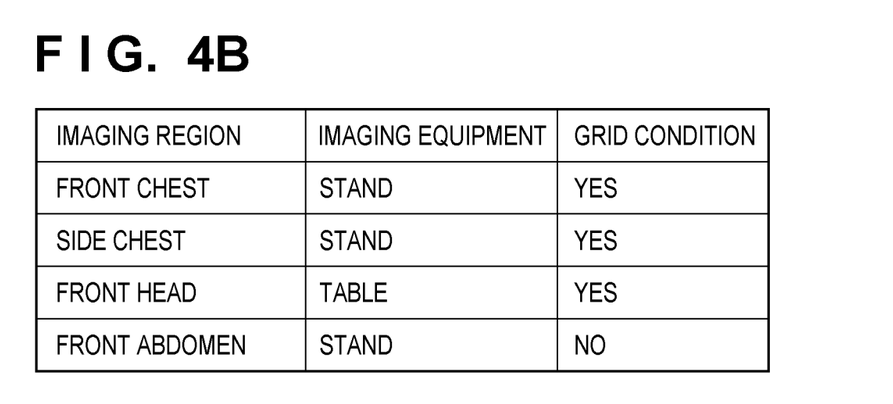

The sensor assignment unit 204 can take into consideration information other than the remaining battery level in the assignment of wireless sensors. In the case where information containing a grid condition (condition indicating whether or not to perform imaging using a grid for removing scattered X-rays) as shown in FIG. 4B is obtained, the sensor assignment unit 204 can also assign a wireless sensor to a combination of the grid condition and the imaging equipment. In this case, the sensor assignment unit 204 assigns wireless sensors in consideration of the three cases "stand+with grid", "table+with grid", and "stand+without grid". Accordingly, the presence or absence of a grid of a wireless sensor (wireless cassette) contained in the sensor information is also taken into consideration. At that time, more efficient imaging is possible by performing not only the process that assigns wireless sensors but also a process that switches as appropriate the imaging order according to given conditions such as the equipment to be used and the presence or absence of a grid. For example, in the above-described example, if the imaging order is switched based on the imaging equipment, the order "stand+with grid", "stand+without grid", and then "table+with grid" is obtained. If the imaging order is determined based on the grid condition, the imaging order "stand+with grid", "table+with grid", and then "stand+without grid", or "stand+without grid", "stand+with grid", and then "table+with grid" is automatically determined.

Figure 4C:
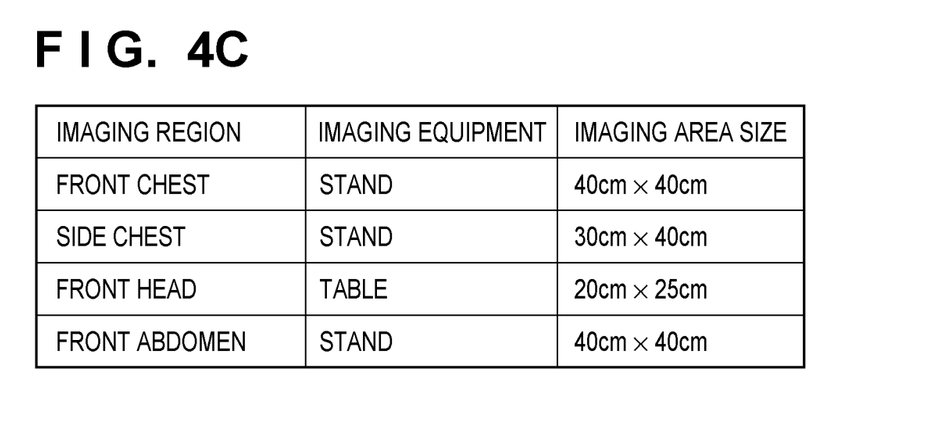
Figure 5B:
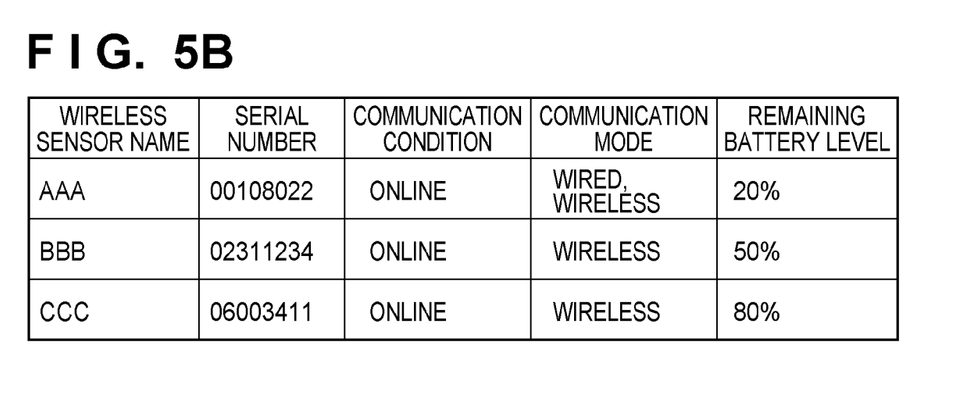
Figure 5C:
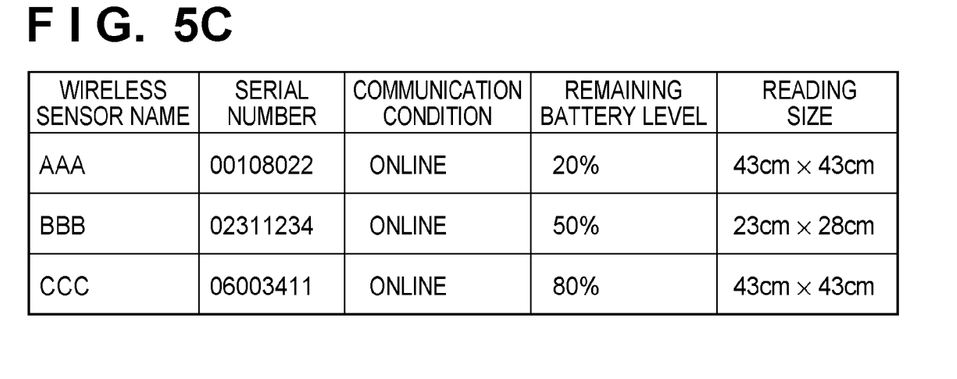

Moreover, sensor assignment can be controlled using the imaging area size. For example, the case will be assumed in which the information containing the imaging area size as shown in FIG. 4C is obtained in step S301 and the information in FIG. 5C is obtained in step S302. In this case, assignment is performed such that a wireless sensor having an imaging area size that is equal to or larger than the size of an imaging area is assigned to that imaging area. The assignment rule for this case is desirably such that the imaging order is determined for a combination of the imaging area size and the imaging equipment. That is to say, two area sizes consisting of 40 cm×40 cm and 30 cm×40 cm are associated with a stand, and, in this case, a sensor CCC having the highest remaining battery level and capable of performing imaging of an 40 cm×40 cm area (reading size 43 cm×43 cm) is assigned to the stand. Meanwhile, only one area size consisting of 20 cm×25 cm is associated with a table, and, thus, a sensor BBB capable of performing imaging of this size (reading size 23 cm×28 cm) is assigned to the table. Here, as the imaging condition indicated by the examination information, not only the conditions shown in FIGS. 4B and 4C but also a combination of information on the grid condition and the imaging area size for imaging an imaging region of the object and the conditions shown in FIG. 4A may be used.

Figure 6:
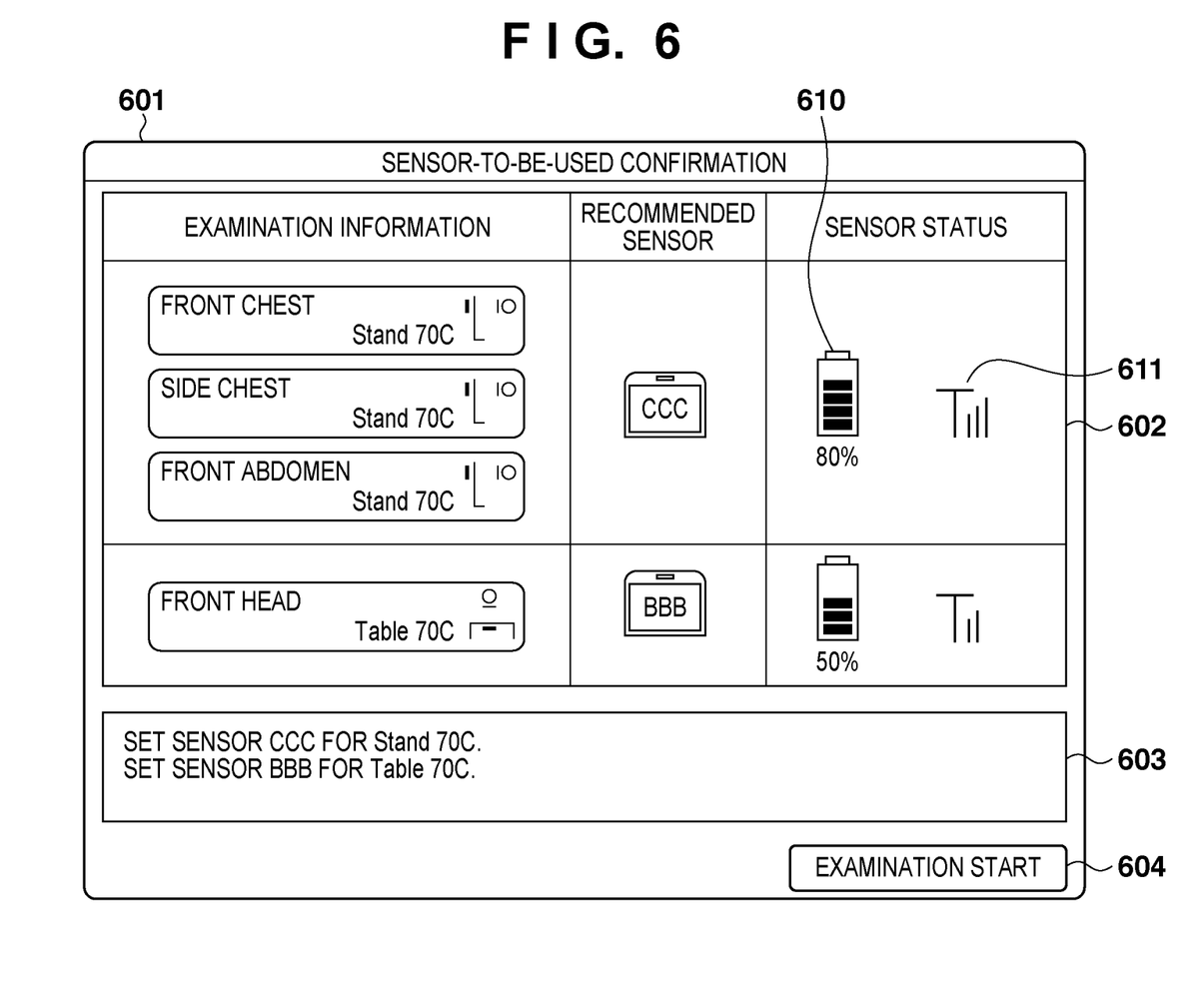
FIG. 6 is a view illustrating a GUI of the X-ray imaging apparatus according to the first embodiment as an example.

Hereinafter, a GUI (sensor-to-be-used confirmation window) for confirming sensor assignment of this embodiment will be described as an example with reference to FIG. 6. A sensor-to-be-used confirmation window 601 is displayed after the examination information has been input and an instruction to start the examination has been given. An area 602 is an area that displays wireless sensors having the highest priority order for assignment (recommended sensors) for imaging regions and imaging equipment contained in the examination information and the statuses of the sensors. The display example in FIG. 6 shows that a wireless sensor is assigned to the examination information shown in FIG. 4A. Furthermore, at the same time, a battery status 610 of each wireless sensor, a wireless communication reception 611, and the like are also displayed. An area 603 is an area that displays an instruction message for the operator. An instruction for the operator indicating which wireless sensor is to be used for imaging under the imaging condition indicated by the examination information is specifically displayed in text information (text). An instruction message for prompting the operator to use the wireless sensor CCC (FIG. 5A) for use of the equipment "Stand 70C" for imaging is displayed. Furthermore, an instruction message for prompting the operator to use the wireless sensor BBB (FIG. 5A) for use of the equipment "Table 70C" is displayed. Then, when the operator selects and presses an examination start button 604, an examination (X-ray imaging) is started.

If assignment and confirmation of usable wireless sensors are performed in advance before starting an examination with reference to the GUI displayed in FIG. 6, the risk that a sensor switching operation has to be performed after starting the examination can be reduced. Thus, even in a state where a plurality of wireless sensor units are usable in the X-ray imaging apparatus, a proper sensor is automatically determined in advance for each imaging operation merely by specifying an imaging technique. Thus, the number of sensor switching operations performed after starting the examination is reduced, and an improvement in the examination throughput can be expected. Furthermore, the risk of keeping patients waiting for sensors to be switched is also reduced, and, thus, a reduction in the disadvantages for patients also can be expected.

Second Embodiment

When using an X-ray imaging apparatus in an examination room, the possibility that a sensor is used with a stand or a table increases. If there is a plurality of sensors to be used, the number of sensor switching operations can be reduced and the efficiency can be increased by assigning sensors respectively to the stand and the table. Meanwhile, in the case of a mobile cart, one wireless sensor is mounted on a mobile cart, and imaging is performed while moving the cart between hospital rooms. Accordingly, it is convenient that assignment is performed such that one wireless sensor is used for each imaging operation even when a plurality of wireless sensors have been registered into a system. Thus, the X-ray imaging apparatus according to this embodiment includes, as a functional constituent element, an operation mode setting unit that sets a use environment in which the X-ray imaging apparatus is used, to either an examination room mode or a mobile cart mode. More optimal sensor assignments can be performed by changing a sensor assignment rule according to the settings by the operation mode setting unit.

Figure 7:
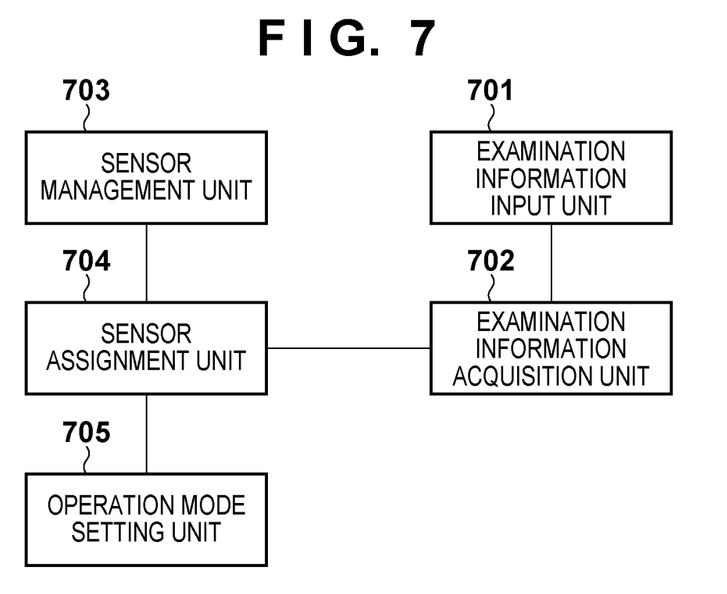
FIG. 7 is a functional configuration diagram of an X-ray imaging apparatus according to a second embodiment.

Hereinafter, a functional configuration of the X-ray imaging apparatus according to the second embodiment will be described with reference to FIG. 7. An examination information input unit 701, an examination information acquisition unit 702, a sensor management unit 703, and a sensor assignment unit 704 are similar to the functional constituent elements described in FIG. 2, and, thus, a description thereof is omitted. The functional configuration shown in FIG. 7 is obtained by adding an operation mode setting unit 705 to the functional configuration described in FIG. 2. The operation mode setting unit 705 sets the mode to either an examination room mode in which imaging is performed using the X-ray imaging apparatus in an examination room or a mobile mode in which imaging is performed on a mobile cart. For example, through a setting screen (not shown) displayed by the operation mode setting unit 705 during installation of the X-ray imaging apparatus, the operator can set the mode to either the examination room mode or the mobile mode. The setting of the mode to either the examination room mode or the mobile mode can be changed anytime. The operation mode setting unit 705 can switch the already set mode upon receiving an instruction to change the setting.

Figure 8:
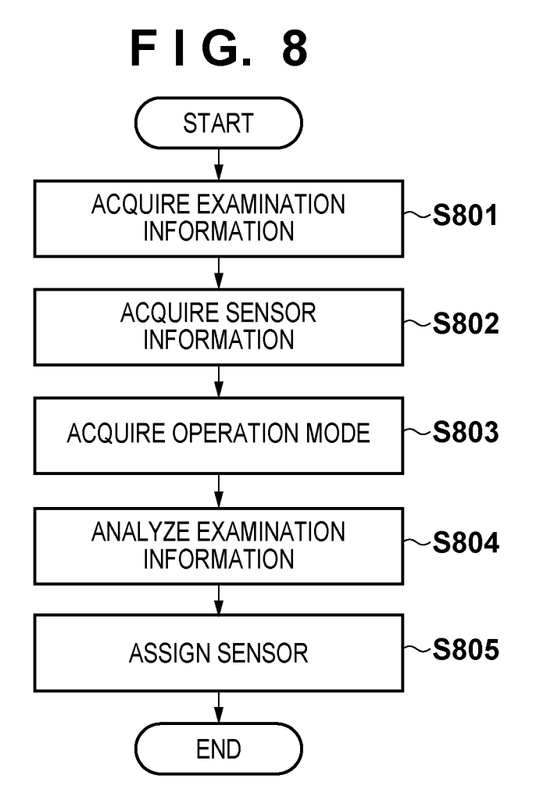
FIG. 8 is a chart illustrating an operation flow of the X-ray imaging apparatus according to the second embodiment.

Next, an operation flow of the X-ray imaging apparatus of this embodiment will be described with reference to FIG. 8. This processing is performed under the overall control of the control unit 101. FIG. 8 shows a processing procedure from acquisition of examination information to assignment of sensors. The operation flow shown in FIG. 8 is obtained by inserting step S803 (operation mode acquiring step) between step S302 (sensor information acquiring step) and step S303 (examination information analyzing step) in FIG. 3.

In step S801, the examination information acquisition unit 702 acquires examination information. Subsequently, in step S802, the sensor assignment unit 704 acquires sensor information managed by the sensor management unit 703.

Subsequently, in step S803, the operation mode setting unit 705 acquires information indicating the operation mode (the examination room mode in which imaging is performed in an examination room or the mobile mode in which imaging is performed on a mobile cart) set in advance in the X-ray imaging apparatus.

Note that the processing procedure of steps S801 to S803 may be in any order, as long as all pieces of information are acquired before the examination information analyzing step S804. Next, in step S804, the sensor assignment unit 704 analyzes the examination information acquired in step S801. In step S805, the sensor assignment unit 704 determines a wireless sensor to be used for each imaging operation based on the information collected in steps S801 to S803 and the analysis result.

For example, in step S803, if the examination room mode indicating use in an examination room as a use environment in which the X-ray imaging apparatus is used is acquired, a wireless sensor having a higher remaining battery level is assigned in descending order of the number of imaging operations to each imaging equipment as described in the first embodiment. That is to say, a priority order of wireless sensor candidates usable for performing X-ray imaging in an imaging condition is assigned to the plurality of managed wireless sensors in descending order of the remaining battery level.

Meanwhile, if the mobile mode indicating use on a mobile cart is acquired, a wireless sensor having the highest remaining battery level is assigned to all imaging operations as a wireless sensor to be used for X-ray imaging, regardless of imaging conditions such as the imaging equipment, the orientation, or the imaging region. In this case, for example, the wireless sensor CCC (wireless sensor with the serial number 06003411) in FIG. 5A is assigned as a wireless sensor to be used for X-ray imaging.

Figure 9:
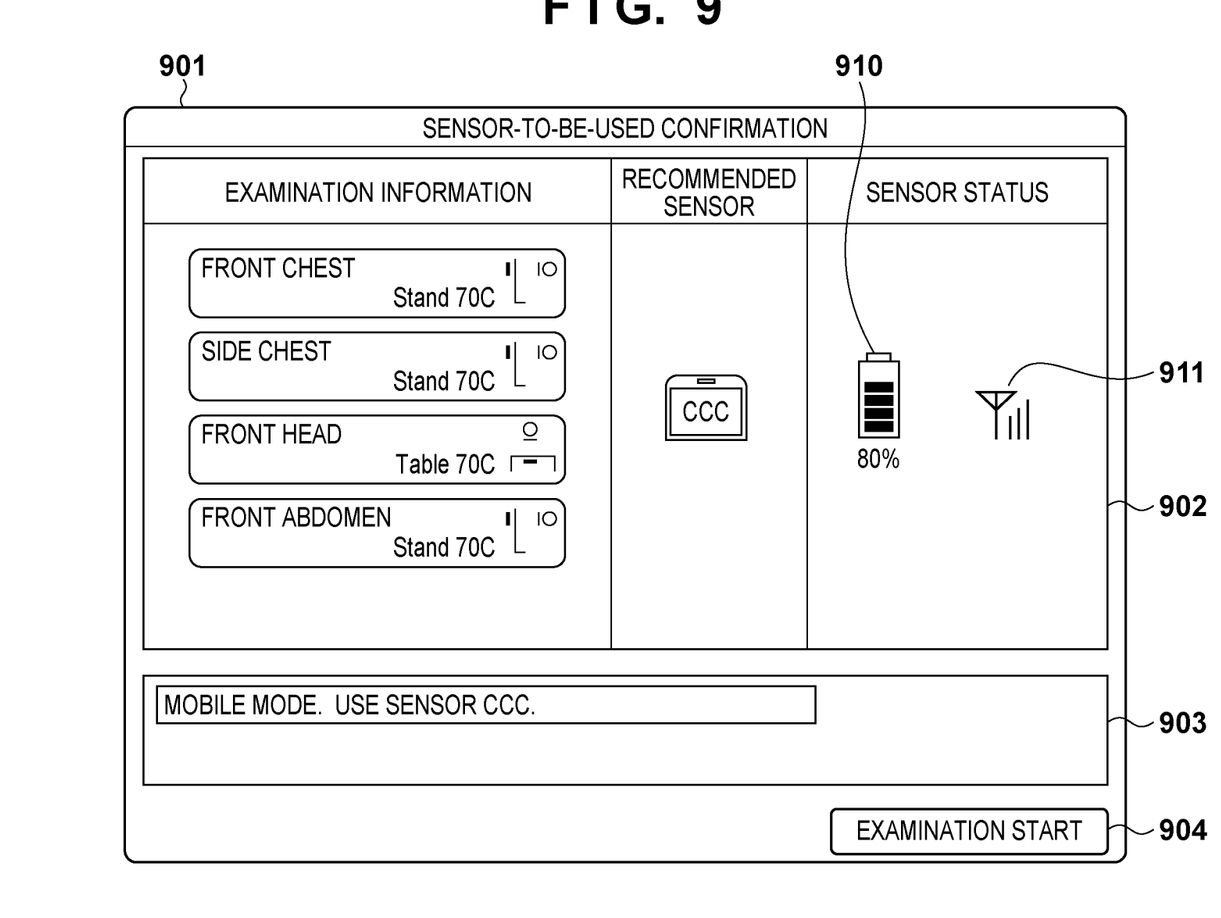
FIG. 9 is a view illustrating a GUI of the X-ray imaging apparatus according to the second embodiment.

Hereinafter, a GUI (sensor-to-be-used confirmation window) for confirming sensor assignment of this embodiment will be described as an example with reference to FIG. 9. A sensor-to-be-used confirmation window 901 is displayed after the examination information has been input and an instruction to start the examination has been given. The sensor-to-be-used confirmation window 901 is an example of a sensor-to-be-used confirmation screen that is displayed on the display unit 105 if the operation mode is the mobile mode. An area 902 is an area that displays wireless sensors having the highest priority order for assignment (recommended sensors) for imaging regions and imaging equipment contained in the examination information and the statuses of the sensors. If the operation mode is the mobile mode, the sensor assignment unit 704 assigns from among a plurality of wireless sensors a wireless sensor having the highest remaining battery level as a wireless sensor to be used for X-ray imaging, regardless of imaging conditions. The display example in FIG. 9 shows that the wireless sensor CCC (FIG. 5A) is assigned to all imaging operations with the examination information shown in FIG. 4A. Furthermore, at the same time, a battery status 910 of a wireless sensor, a wireless communication reception 911, and the like are also displayed. An area 903 is an area that displays an instruction message for the operator. An instruction for the operator indicating which wireless sensor is to use for imaging under the imaging condition indicated by the examination information is specifically displayed in text information (text). A message indicating that the operation mode is the mobile mode and instructing the operator to use the wireless sensor CCC (FIG. 5A) having the highest remaining battery level from among a plurality of wireless sensors is displayed. Then, when the operator selects and presses an examination start button 904, an examination (X-ray imaging) is started.

Note that the acquisition of the information indicating the operation mode in step S803 does not necessarily have to be performed immediately before starting the examination, and may be performed when turning on the X-ray imaging apparatus. For example, the case will be assumed in which the information indicating the operation mode acquired when turning on the X-ray imaging apparatus is information indicating the mobile mode. In this case, a wireless sensor having the highest remaining battery level can be assigned to all imaging operations as a wireless sensor to be used for X-ray imaging, without performing the analysis of the examination information in subsequent steps. Furthermore, an examination can be started with the sensor-to-be-used confirmation screen (FIG. 9) displayed on the display unit 105 when turning on the X-ray imaging apparatus, without displaying the confirmation screen each time starting the examination.

Third Embodiment

If it is determined that there is no wireless sensor that can currently perform communication from the sensor information acquired in step S302 or S802, the sensor assignment unit 204 or 704 cannot acquire the remaining battery level of a wireless sensor. In this case, the sensor assignment unit 204 or 704 can assign a wireless sensor based on the wireless sensor assignment rule (priority order) assigned the last time of use of the X-ray imaging apparatus, and propose the assigned wireless sensor as a recommended sensor. For example, the wireless sensor assignment rule (priority order) assigned the last time of use of the X-ray imaging apparatus is stored in the non-volatile storage device 1015 when turning off the X-ray imaging apparatus. If it is determined that there is no wireless sensor that can currently perform communication when turning on the X-ray imaging apparatus next time, wireless sensor assignment can be performed according to the priority order assigned in the last use stored in the non-volatile storage device 1015.

Furthermore, the sensor assignment units 204 and 704 can control the X-ray imaging apparatus such that an examination is started after a message for prompting the operator to confirm the power and the communication has been displayed prior to the start of the examination, and establishment of communication with all wireless sensors has been confirmed. With such a control, it is reliably assured that the wireless sensors are usable prior to the examination, and, thus, the frequency of the process that turns on wireless sensors or exchanges wireless sensors after starting the examination is reduced.

Fourth Embodiment

A wireless sensor may be provided with not only a wireless connection function but also a wired connection function.

For example, the sensor information acquired in step S302 or S802 contains information indicating a communication mode. From a sensor provided with not only a wireless connection function but also a wired connection function, information indicating that connection is possible in a plurality of communication modes ("wired, wireless") is acquired as shown in FIG. 5B. On the other hand, from a wireless sensor provided only with a wireless connection function, information indicating that connection is possible in a single communication mode ("wireless") is acquired.

The sensor assignment units 204 and 704 can reduce the risk that the battery runs out after starting the examination, by preferentially assigning a sensor determined to be capable of being wire-connected from the communication mode information.

Other Embodiments

Aspects of the present invention can also be realized by a computer of a system or apparatus (or devices such as a CPU or MPU) that reads out and executes a program recorded on a memory device to perform the functions of the above-described embodiment, and by a method, the steps of which are performed by a computer of a system or apparatus by, for example, reading out and executing a program recorded on a memory device to perform the functions of the above-described embodiment. For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-195060, filed Aug. 31, 2010, which is hereby incorporated by reference herein in its entirety.

What is claimed is:

1. An X-ray imaging apparatus that performs X-ray imaging while switching a plurality of wireless sensors according to an imaging condition of an object, comprising:
   an acquisition unit configured to acquire examination information indicating the imaging condition of the object;
   a management unit configured to manage, as sensor information, remaining battery levels of the plurality of wireless sensors that have been registered;
   a control unit configured to assign a priority order of wireless sensor candidates usable for performing the X-ray imaging according to the imaging condition indicated in the examination information acquired by said acquisition unit to the plurality of wireless sensors, in descending order of the remaining battery levels managed by said management unit; and
   an imaging unit configured to perform the X-ray imaging of the object using wireless sensors sequentially consisting of those in descending order of the priority order assigned by said control unit up to a wireless sensor having a preset order number, as determined according to the imaging condition.

2. The X-ray imaging apparatus according to claim 1, further comprising a setting unit configured to set a mode in which the X-ray imaging apparatus is used in one of an examination room mode, in which imaging is performed in an examination room, and a mobile mode, in which imaging is performed on a mobile cart,
   wherein, if the examination room mode is set, said control unit assigns a priority order of wireless sensor candidates usable for performing the X-ray imaging according to the imaging condition to the plurality of wireless sensors managed by said management unit, in descending order of the remaining battery levels, and
   if the mobile mode is set, said control unit assigns a wireless sensor having a highest remaining battery level from among the plurality of wireless sensors as a wireless sensor to be used for the X-ray imaging, regardless of the imaging condition.

3. The X-ray imaging apparatus according to claim 1, further comprising a storage unit configured to store the priority order of the wireless sensors assigned the last time of use of the X-ray imaging apparatus, when turning off the X-ray imaging apparatus,
   wherein the sensor information managed by said management unit contains information indicating a communication condition of whether or not the wireless sensors can perform wireless communication, and
   if it is determined from the information indicating the communication condition that there is no wireless sensor that can currently perform communication when turning on the X-ray imaging apparatus, said control unit performs wireless sensor assignment according to the priority order assigned in the last use, as stored in said storage unit.

4. The X-ray imaging apparatus according to claim 1, wherein the sensor information managed by said management unit contains information indicating whether or not communication via wired connection can be performed in addition to wireless communication, and
   said control unit performs assignment such that a priority order of a wireless sensor that can perform communication via the wired connection is higher than a priority order of a wireless sensor that cannot perform communication via the wired connection.

5. The X-ray imaging apparatus according to claim 1, further comprising a display unit configured to display a result of the assignment performed by said control unit.

6. The X-ray imaging apparatus according to claim 1, wherein the imaging condition contains information on an imaging region of the object and imaging equipment to be used for the imaging of the imaging region.

7. The X-ray imaging apparatus according to claim 6, wherein the imaging condition further contains at least one of a grid condition of whether or not to perform imaging using a grid for removing a scattered X-ray and an imaging area size for the imaging of the imaging region of the object.

8. An X-ray imaging apparatus that performs X-ray imaging while switching a plurality of wireless sensors according to an imaging condition of an object, comprising:
   an acquisition unit configured to acquire examination information indicating the imaging condition of the object;
   a management unit configured to manage, as sensor information, remaining battery levels of the plurality of wireless sensors that have been registered; and
   a control unit configured to assign a priority order of wireless sensor candidates usable for performing the X-ray imaging according to the imaging condition indicated in the examination information acquired by said acquisition unit to the plurality of wireless sensors, in descending order of the remaining battery levels managed by said management unit.

9. An X-ray imaging apparatus that performs X-ray imaging while switching a plurality of wireless sensors according to an imaging condition of an object, comprising:
   an acquisition unit configured to acquire examination information indicating the imaging condition of the object;
   a management unit configured to manage, as sensor information, remaining battery levels of the plurality of wireless sensors that have been registered;
   a control unit configured to assign a priority order of wireless sensor candidates usable for performing the X-ray imaging according to the imaging condition indicated in the examination information acquired by said acquisition unit to the plurality of wireless sensors, in descending order of the remaining battery levels managed by said management unit; and
   a display unit configured to display the priority order of the wireless sensor candidates assigned by said control unit.

* * * * *